(12) United States Patent
Trout, III et al.

(10) Patent No.: US 6,409,757 B1
(45) Date of Patent: Jun. 25, 2002

(54) METHOD AND APPARATUS FOR SUPPORTING A GRAFT ASSEMBLY

(75) Inventors: Hugh H. Trout, III, Bethesda, MD (US); Howard M. Tanner, Logan, UT (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/396,513

(22) Filed: Sep. 15, 1999

(51) Int. Cl.$^7$ .................................................. A61F 2/06
(52) U.S. Cl. ..................................... 623/1.36; 623/1.35
(58) Field of Search ............................... 623/1.11, 113, 623/1, 1.15, 1.32, 1.35, 1.36

(56) References Cited

U.S. PATENT DOCUMENTS

| | | | | |
|---|---|---|---|---|
| 4,545,082 A | * | 10/1985 | Hood | 623/1 |
| 5,578,071 A | * | 11/1996 | Parodi | 623/1 |
| 5,628,783 A | * | 5/1997 | Quiachon et al. | 623/1 |
| 5,693,087 A | * | 12/1997 | Parodi | 623/1 |
| 5,720,776 A | * | 2/1998 | Chuter et al. | 623/1 |
| 5,723,003 A | * | 3/1998 | Winston et al. | 623/1 |
| 5,782,904 A | * | 7/1998 | White et al. | 623/1 |
| 6,036,725 A | * | 3/2000 | Aellanet | 623/1 |
| 6,129,756 A | * | 10/2000 | Kugler et al. | 623/1.27 |
| 6,176,875 B1 | * | 1/2001 | Lenker et al. | 623/1.49 |
| 6,248,128 B1 | * | 6/2001 | Berry et al. | 623/1.17 |
| 6,273,909 B1 | * | 8/2001 | Kugler et al. | 623/1.13 |

* cited by examiner

*Primary Examiner*—Corrine McDermott
*Assistant Examiner*—Hieu Phan
(74) *Attorney, Agent, or Firm*—John N. Coulby; Mark W. Rygiel; Collier Shannon Scott, PLLC

(57) ABSTRACT

A graft repair system for use in the repair of an aneurysm within a vessel is disclosed. The graft repair system includes a graft assembly and a support assembly for supporting the graft assembly within the vessel. The graft assembly may include a tubular portion having proximal and distal ends. The graft assembly may be bifurcated. The graft assembly may further comprise a distal graft assembly. The support assembly includes at least one attachment assembly for attaching the graft assembly to a vessel wall. The support assembly further includes a connecting assembly for connecting the attachment assembly to the proximal end of the graft assembly, such that the attachment assembly extends cephalad from the proximal end of the graft assembly. The support device further includes a securing assembly for securing the connecting assembly to the proximal end of the graft assembly.

18 Claims, 4 Drawing Sheets

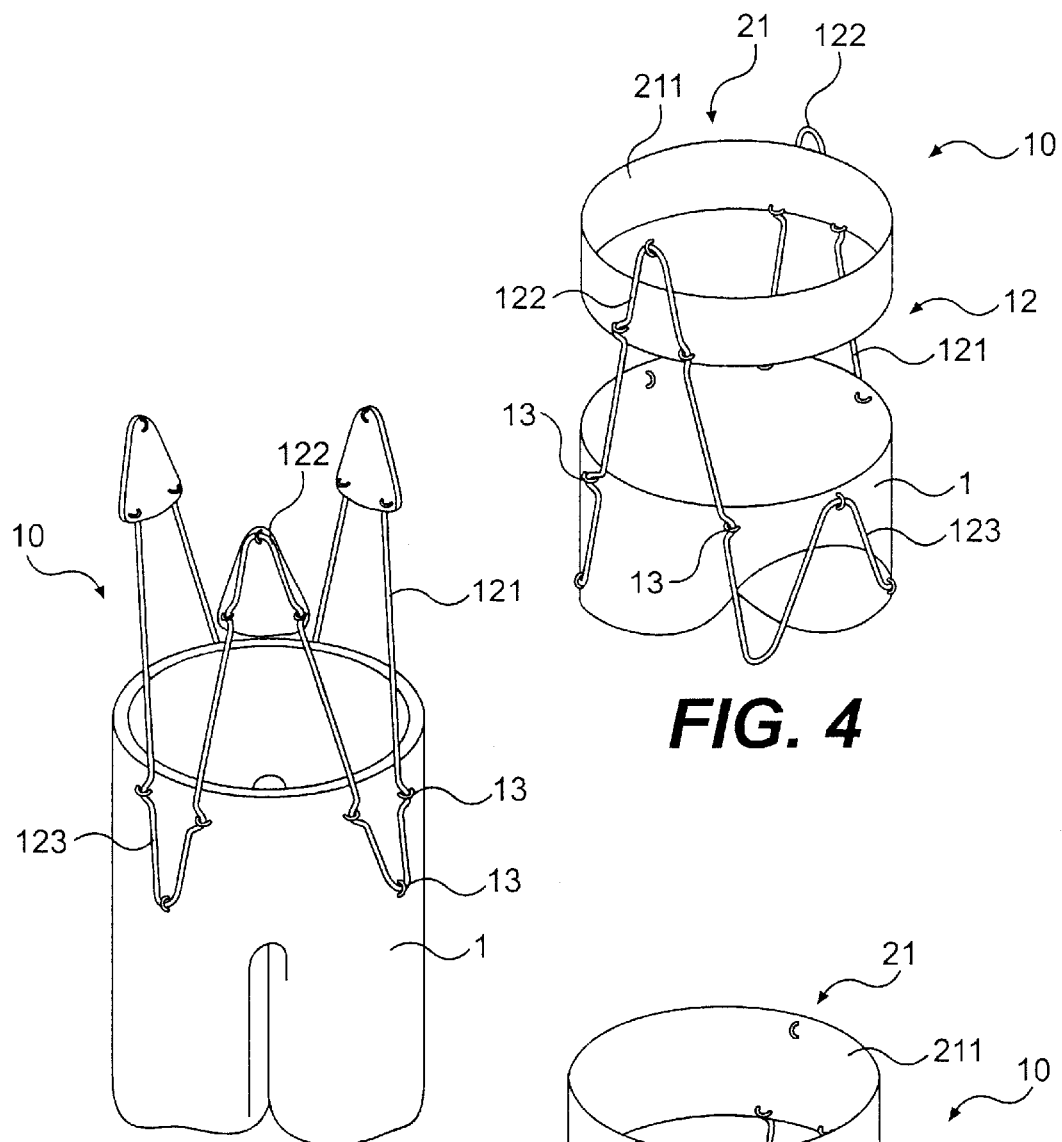
FIG. 3
FIG. 4
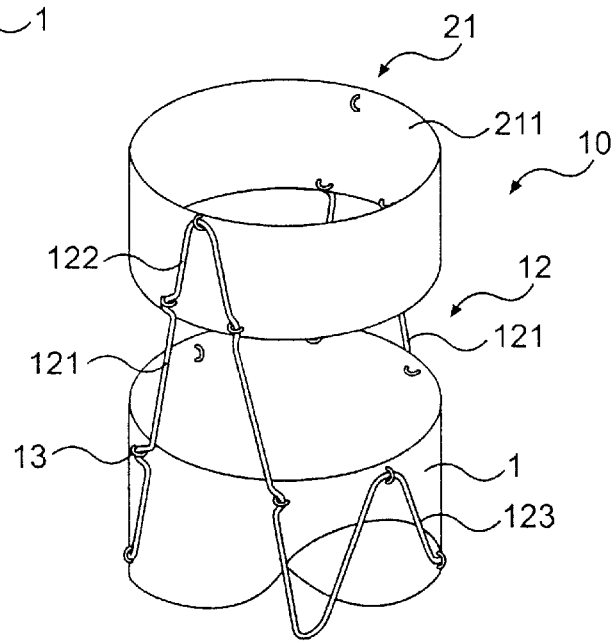
FIG. 5

METHOD AND APPARATUS FOR SUPPORTING A GRAFT ASSEMBLY

FIELD OF THE INVENTION

The present invention relates to a method and apparatus for supporting a graft assembly during the repair of an abdominal aortic aneurysm using a novel support device to prevent migration of the graft assembly within the abdominal aorta.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm as no statistical benefit exists to do so.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the abdominal wall (i.e., abdominal aorta). A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an abdominal aortic aneurysm without the attendant risks of intra-abdominal surgical intervention. Although techniques have been developed that may reduce the stress, morbidity, and risk of mortality associated with surgical intervention to repair aortic aneurysms, none of the prior art systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta abutting the aneurysm to ensure attachment of the graft. The proximal aortic neck (i.e., above the aneurysm) is usually sufficient to support a graft's attachment means. However, when an aneurysm is located near the iliac arteries, there may be an ill-defined neck or no neck below the aneurysm. Such an ill-defined neck would have an insufficient amount of healthy aortic tissue to which to successfully attach a graft. Furthermore, much of the abdominal aortic wall may be calcified making it extremely difficult to attach a graft thereto.

There are a number of shortcomings with the presently available graft products and their fixation within the abdominal aorta. Although sizing of "tube" or "bifurcated" grafts is radiographically assessed prior to surgery, it is necessary for the surgeon to have a large selection of graft lengths and diameters on hand to ensure an appropriate surgical outcome. Additional shortcomings include the placement of a "circular" profile graft with an associated fixation device within an essentially "ovoid" profiled vessel and the use of attachment means which fasten only to the insubstantial, structurally compromised (diseased) intima and media layers (i.e., strata) of the vessel wall. Research has shown yet another problem which indicates that the necks of the post-surgical aorta increase in size for approximately twelve months, regardless of whether the aneurysm experiences dimensional change. This phenomenon can result in peri-graft leaks and graft migration.

Graft migration is a significant problem affecting many of the grafts available within the intraluminal abdominal aortic aneurysm market. These grafts are attached within the aortic lumen at a proximal positioning by means of stents, which provide outward radial forces thereby forcing the graft into the lumen wall. In some instances barbs, part of the stent fabrication, provide additional fixation. There are numerous problems with this design approach. The stent of the aforementioned concept is expanded into a compromised vessel having questionable mechanical integrity. Second, the proximal distal neck has been shown to expand immediately post operatively and for a period of twelve months thereafter causing the graft to detach from or loosen with respect to the lumen. Finally, the barbs of the stent product are of questionable merit as they fasten into the intima of the lumen wall which has compromised mechanical integrity.

By comparison, the present inventors developed a graft assembly disclosed in U.S. patent application Ser. No. 08/896,415, filed Jul. 18, 1997, entitled "Method and Apparatus for the Surgical Repair of Aneurysms," the disclosure of which is incorporated herein by reference, that is positively fastened to the adventia, the outermost of three strata within the vessel wall, having appropriate mechanical integrity. The grafts disclosed in U.S. patent application Ser. No. 08/896,415 are not comprised by expansion of the distal neck. The present invention addresses the short comings of the prior art grafts. The present invention also enhances the performance of the graft assembly disclosed in U.S. patent application Ser. No. 08/896,415.

OBJECTS OF THE INVENTION

It is therefore an object of the present invention to overcome the above-identified shortcomings of the prior art.

It is another object of the present invention to provide a support device for a graft assembly.

It is another object of the present invention to provide a support device for a graft assembly to support the graft assembly within a vessel.

It is another object of the present invention to provide a support device for a graft assembly that supports the graft assembly to prevent graft migration in a cephalad/caudad direction within the vessel.

It is another object of the present invention to provide a support device for a graft assembly to provide additional securement points for securing the graft assembly to the vessel wall.

It is another object of the present invention to provide a support device for a graft assembly to reduce the impact of vessel expansion on the graft assembly when located within the vessel.

It is another object of the present invention to provide a support device for a graft assembly within a vessel without impeding blood flow arteriorly (towards the intestine).

It is another object of the present invention to provide a support device for a graft assembly within a vessel without impeding blood flow posteriorly (towards the spine).

It is another object of the present invention to provide a support device for a graft assembly having at least one attachment assembly that is capable of being secured within the thoracic or suprarenal aorta.

It is another object of the present invention to provide a support device for a graft assembly that does not block blood flow to and from the renal arteries.

It is another object of the present invention to provide a support device for a graft assembly formed from a biocompatible material.

It is another object of the present invention to provide a support device for a graft assembly having at least one attachment assembly to prevent graft migration in a cephalad/caudad direction.

It is another object of the present invention to provide a graft repair system for use in the surgical repair of aneurysms within a vessel.

It is another object of the present invention to provide a graft repair system having a graft assembly and a support assembly to prevent migration of the graft assembly within a vessel.

SUMMARY OF THE INVENTION

The prevent invention is directed to a support device for supporting a graft assembly within a vessel. The graft assembly includes a tubular portion having a proximal end. The support device in accordance with the present invention includes at least one attachment assembly for attaching the graft assembly to a vessel wall of the vessel. The at least one attachment assembly is capable of being secured to the vessel wall. The support device further includes a connecting assembly for connecting the attachment assembly to the proximal end of the graft assembly, such that the attachment assembly extends from the proximal end of the graft assembly. The support device further includes a securing assembly for securing the connecting assembly to the proximal end of the graft assembly.

In accordance with the present invention, the at least one attachment assembly may include at least one attachment pad. Alternatively, the at least one attachment assembly may include an attachment tube or collar. The at least one attachment assembly may be formed from a biocompatible material such as, Gore-Tex®.

In accordance with the present invention, the connecting assembly may include a support assembly that extends from the at least one attachment assembly to the proximal end of the graft assembly. The support assembly may include at least one support leg that extends from the attachment assembly to the proximal end of the graft assembly.

In accordance with the present invention, the attachment assembly may include a plurality of attachment assemblies. The at least one support leg extends to each of the plurality of attachment assemblies.

The present invention is also directed to a graft repair system for use in the repair of aneurysm within a vessel. The graft repair system includes a graft assembly and a support device for supporting the graft assembly within the vessel. The graft assembly may include a tubular portion, a proximal end and a distal end. The graft assembly may be a bifurcated graft assembly. The graft assembly may further comprise a flexible attachment assembly extending from the distal end of the graft assembly. The support device in accordance with the present invention includes at least one attachment assembly for attaching the graft assembly to a wall of the vessel. The at least one attachment assembly is capable of being secured to the vessel wall. The support device further includes a connecting assembly for connecting the attachment assembly to the proximal end of the graft assembly, such that the attachment assembly extends from the proximal end of the graft assembly. The support device further includes a securing assembly for securing the connecting assembly to the proximal end of the graft assembly.

BRIEF DESCRIPTION OF THE DRAWINGS

The invention will now be described in conjunction with the following drawings in which like reference numerals designate like elements and wherein:

FIG. 3 is a perspective view of a graft assembly having a graft support device in accordance with another embodiment of the present invention;

FIG. 4 is a perspective view of a graft assembly having a graft support device in accordance with another embodiment of the present invention;

FIG. 5 is a perspective view of a graft assembly having a graft support device in accordance with another embodiment of the present invention;

DETAILED DESCRIPTION OF PREFERRED EMBODIMENTS

The following descriptions of the preferred embodiments of the present invention are described, for purpose of example, in connection with the repair of an abdominal aortic aneurysm. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

Figure 1:
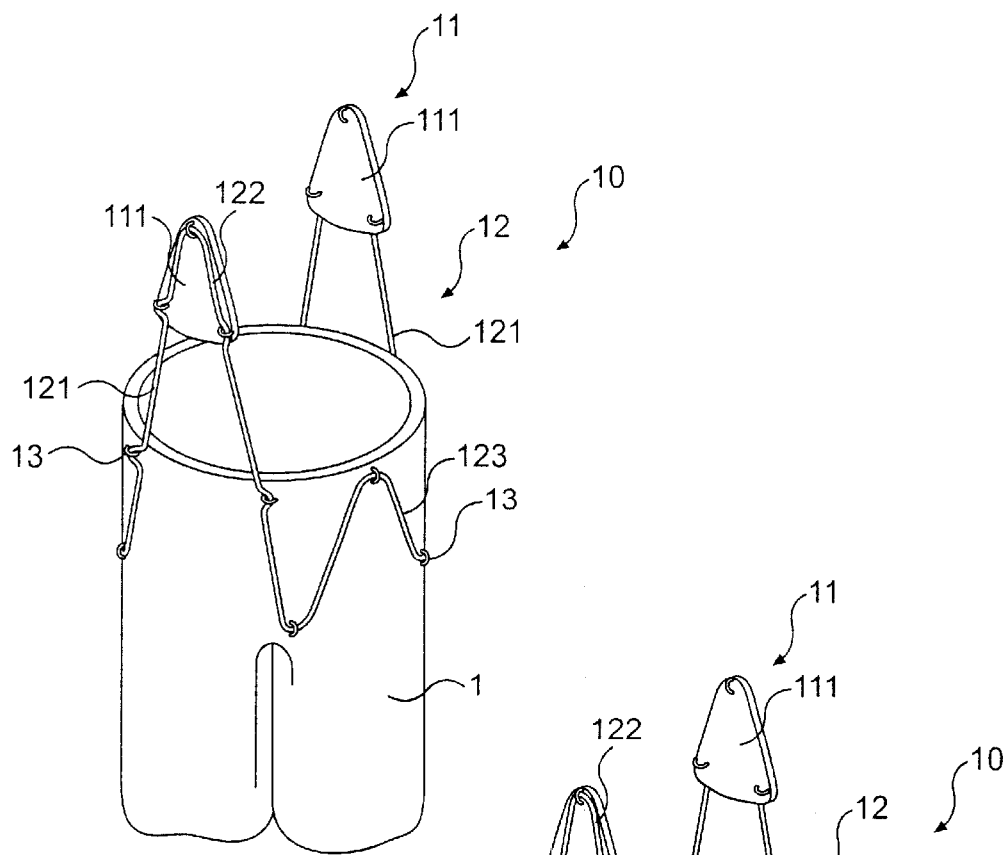
FIG. 1 is a perspective view of a graft assembly having a graft support device in accordance with an embodiment of the present invention.

A support device 10 is illustrated in FIG. 1 in accordance with an embodiment of the present invention. The support device 10 is secured to a graft assembly 1. The support device 10 includes at least one attachment assembly 11. In accordance with the embodiment of the present invention illustrated in FIG. 1, the attachment assembly 11 includes a pair of attachment pads 111. The attachment pads 111 are adapted to be positioned on opposing sides of the proximal end of the graft assembly 1. Each pad 111 is preferably formed from Gore-Tex® or equivalent biocompatible material including but not limited to Dacron®. It will be apparent to those skilled in the art that various modifications and variations can be made in the construction and configuration of the present invention without departing from the scope or spirit of the invention. Each attachment assembly 11 is adapted to be secured to a vessel wall using an appropriate fastener as disclosed for example in U.S. patent application Ser. No. 08/896,415, filed Jul. 18, 1997, entitled "Method and Apparatus for the Surgical Repair of Aneurysms," U.S. patent application Ser. No. 08/958,524, filed Oct. 27, 1997, entitled "Fasteners for Use in the Surgical Repair of Aneurysms" and U.S. patent application Ser. No. 09/108,191, filed Jul. 1, 1998, entitled "Method and Apparatus for the Surgical Repair of Aneurysms," the disclosures of which are incorporated herein by reference.

Figure 7:
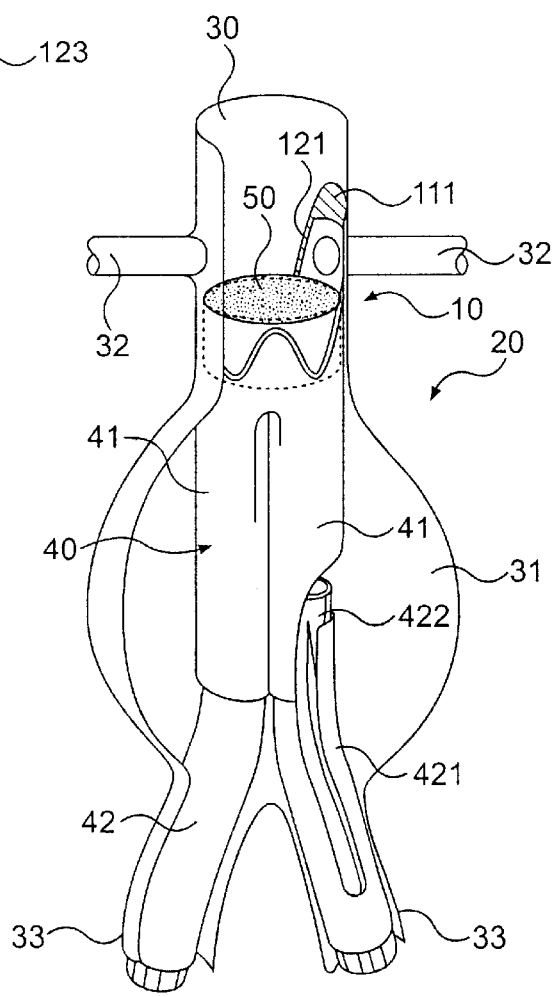
FIG. 7 is a schematic view of a graft repair system in accordance with the present invention positioned within a vessel.
Figure 9:
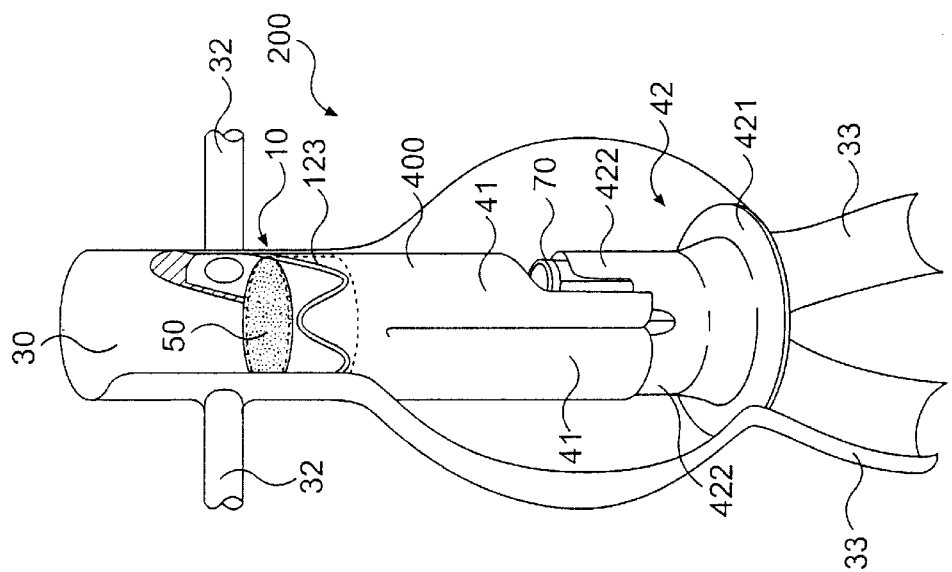
FIG. 9 is a schematic view of another graft repair system in accordance with the present invention positioned within a vessel.
Figure 8:
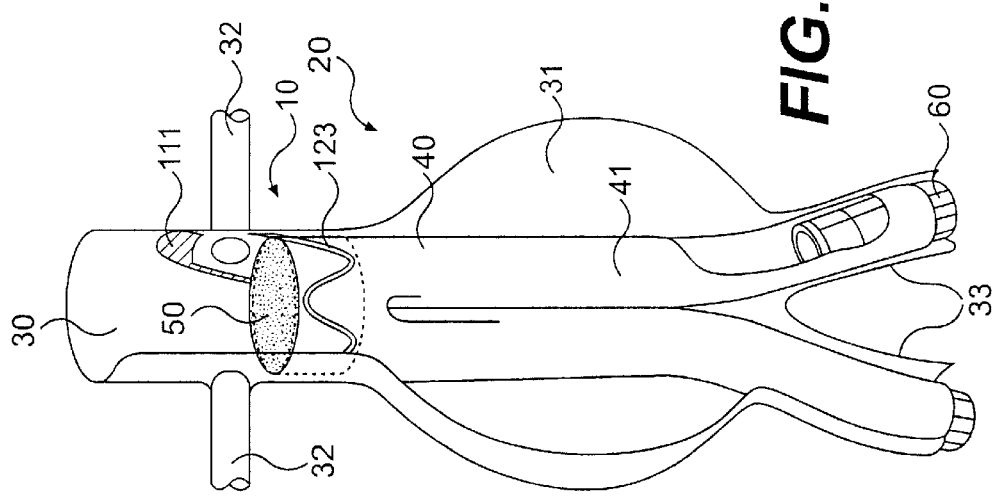
FIG. 8 is a schematic view of another graft repair system in accordance with the present invention positioned within a vessel.

A connecting assembly 12 is connected to the at least one attachment assembly 11. The connecting assembly 12 positions the at least one attachment assembly 11 such that it is spaced from the proximal end of the graft assembly 1. This arrangement does not impede the flow of blood within the vessel. Furthermore, this arrangement does not block the flow of blood to the renal arteries as shown in FIGS. 7–9. The connecting assembly 12 includes a support system having at least one support leg 121 which extends from the proximal end of the graft assembly 1 to the attachment assembly 11. Each attachment assembly 11 is secured to the connecting assembly 12 at an attachment portion 122.

In the embodiment illustrated in FIG. 1, the attachment pads 111 have a tailored configuration to conform to the shape of the attachment portion 122. Each attachment pad 111 is attached to the attachment portion 122 using appropriate stitches 123. The attachment 111 may be secured to the attachment portion 122 by other suitable means. For example, a suitable adhesive may be used to bond the attachment position 122 to the attachment pad 111. Alternatively, the attachment pad 111 may be formed around the attachment portion 122. The attachment portion 122 may be woven through apertures in the proximal end of the graft assembly 1.

The support legs 121 of the connecting assembly 12 are interconnected through a securement assembly 123 adjacent the proximal end of the graft assembly 1. A securing assembly 13 attaches the securement assembly 123 to the proximal end of the graft assembly 1. The securing assembly 13 may comprise a plurality of stitches, as shown in FIG. 1. The present invention, however, is not limited to the use of stitches, rather other means for securing the connecting assembly 12 to the proximal end of the graft assembly 1 are considered to be well within the scope of the present invention. For example, suitable adhesive may be used to bond the securement assembly 123 to the proximal end of the graft assembly 1. The proximal end of the graft assembly 1 may be formed around the securement assembly 123 such that the assembly 123 is positioned within the vessel wall. Alternatively, the securement assembly 123 may be woven through apertures in the proximal end of the graft assembly 1.

The assembly 12 may be formed from a single strand of nitinol wire used for both its thermal and superelastic attributes in the manner illustrated in FIG. 1. Other materials are considered to be well within the scope of the present invention, including but not limited to sutures and other biocompatible materials. Additionally, the connecting assembly 12 may be formed of a braid of several strands of wire.

Figure 2:
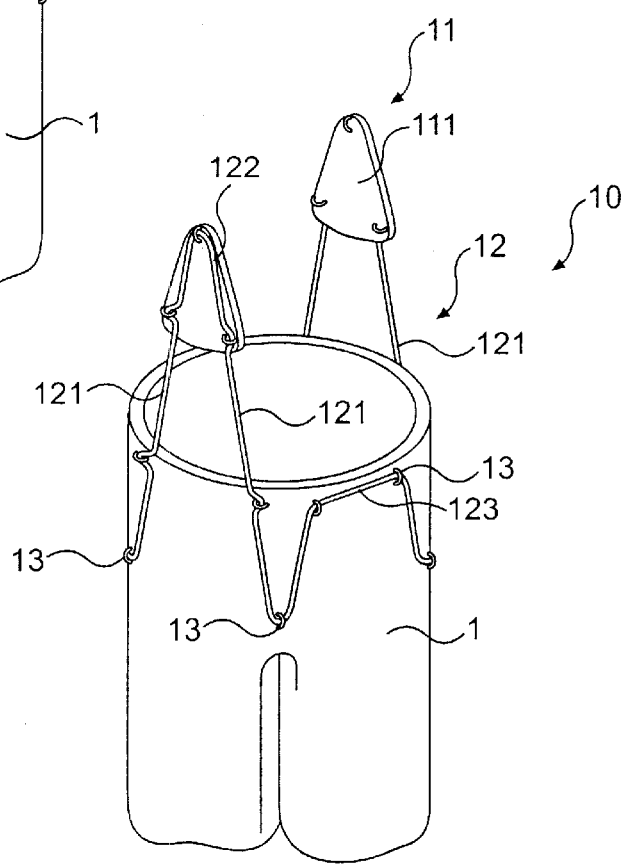
FIG. 2 is a perspective view of a graft assembly having a graft support device in accordance with another embodiment of the present invention.

FIG. 2 illustrates a variation of the support device 10 depicted in FIG. 1. In particular, the securement assembly 123 of the connecting assembly 12 has a different configuration to permit additional points of contact for the securing assembly 13.

FIG. 3 illustrates another embodiment of the support device 10 according to the present invention having at least three attachment pads 111. The present invention, however, is not limited to three attachment pads 111. It is contemplated that three or more attachment pads are considered to be well within the scope of the present invention.

FIG. 4 illustrates another variation of the support device 10 according to the present invention. The attachment assembly 21 includes an attachment collar 211. The attachment collar 211 is preferably formed from Gore-Tex® or equivalent biocompatible material. In the embodiment illustrated in FIG. 4, the attachment portion 122 of the connecting assembly 12 extends above the attachment collar 211. In contrast to the embodiment disclosed in FIG. 5, the attachment portion 122 of the connecting assembly 12 does not extend above the attachment collar 211.

Figure 6:
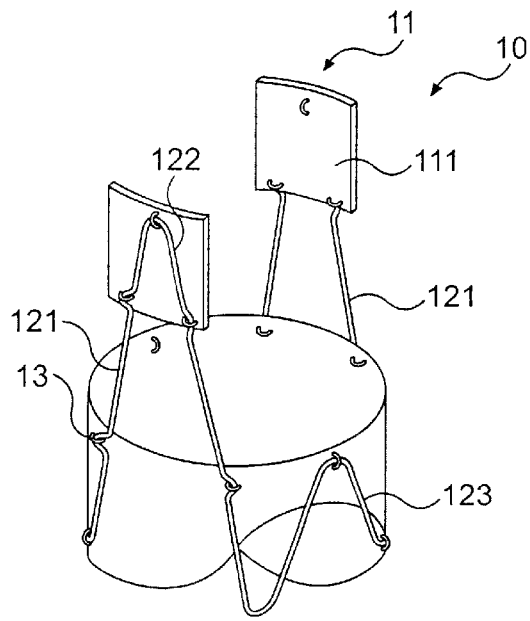
FIG. 6 is a perspective view of a graft assembly having a graft support device in accordance with another embodiment of the present invention.

FIG. 6 illustrates another variation of the support device 10 of FIG. 1. In this embodiment, the attachment pads 111 are not tailored to the shape of the attachment portion 122 of the connecting assembly 12.

FIG. 7 illustrates a graft repair system 20 in accordance with the present invention. The graft repair system 20 is adapted to be located within a vessel 30 having an aneurysm 31 therein. Renal arteries 32 extend from the vessel 30. Iliac arteries 33 also extend from the vessel 30.

The graft repair system 20 includes a graft assembly 40. The graft assembly 40 may be a bifurcated graft assembly having a pair of tubular legs 41. A support device 10, described above, is secured to the proximal end of the graft assembly 40. A graft covered stent limb or stent covered graft 42 extends from each tubular leg 41 of the graft assembly 40 to an iliac artery 33. The stent limb 42 includes an outer graft component 421 that may be formed from the same material as the graft assembly and an inner stent assembly 422. The inner stent assembly 422 exerts a radial force sufficient to secure one end of the stent limb 42 to one of the tubular legs 41 and at an opposite end, the stented limb 42 to the iliac artery 33.

The proximal end of graft assembly 40 is secured within the vessel 30 using the support device 10. The attachment pads 111 are secured to the vessel wall of the vessel 30 using appropriate fasteners which pass through the attachment pads 111 and the vessel 30. The attachment pads 111 may be secured using the penetration device described in U.S. patent application Ser. No. 08/692,127, entitled "Implantation Device for Aortic Graft, method of Treating Aortic Aneurysm" and U.S. patent application Ser. No. 09/293,175, entitled "Repair Apparatus for Use in Surgical Procedures," the disclosures of which are incorporated herein by reference.

The proximal end of the graft assembly 40 may be further secured using a stent 50 located within the proximal end. Fasteners may also be used to secure the proximal end to the vessel wall.

FIG. 8 illustrates a variation of the graft repair system 20 of FIG. 7. The pair of tubular legs 41 have sufficient length such that each leg 41 extends into the iliac artery 33, as shown in FIG. 8. A stent 60 is then positioned within the end portion of the each leg 41 to secure it to an iliac artery 33.

FIG. 9 illustrates another variation of the graft repair system 200 according to the present invention. The graft repair system 200 includes a graft assembly 400. The graft assembly 400 may be a bifurcated graft assembly having a pair of tubular legs 41. The graft assembly 400 is not limited to a pair of tubular legs 41; rather, a single passageway may be provided. The graft repair system 200 includes a support device 10, described above, which is secured to the proximal end of the graft assembly 400 through the securing assembly 13.

A graft repair system 200 preferably comprises a distal graft attachment assembly 42 having a flexible attachment cuff 421. The attachment cuff 421 is sized to secure the distal graft attachment assembly 42 to the wall of the vessel 1 at the distal end of the vessel 1 adjacent the iliac arteries 33. The distal graft attachment assembly 42 also comprises at least one graft attachment leg, tube or branch 422. The attachment cuff 421 is secured to the wall of the vessel 1 out to the adventitia using a suitable fastener.

After the attachment cuff 421 of the distal graft assembly 42 is firmly secured to the vessel wall, attachment tubes 422 are invaginated from a caudad positioning to a cephalad positioning, as shown in FIG. 9. The legs 41 of the graft assembly 400 are then secured to the attachment legs 422 of the distal graft assembly 42 using suitable connectors, such as, a self-expanding stent 70. The present invention is not limited to a bifurcated graft attachment assembly 42; rather the number of attachment tubes for the graft attachment assembly corresponds to the number of legs 41 of the graft assembly 400.

In the above described embodiments, the graft assemblies are preferably formed from Gore-Tex® or equivalent biocompatible material. It will be apparent to those skilled in the art that various modifications and variations can be made in the construction and configuration of the present invention without departing from the scope or spirit of the invention. For example, in the embodiments mentioned above, other biocompatible materials such as, Dacron®, may be used to form the repair grafts. Thus, it is intended that the present invention cover the modifications and variations of the invention, provided they fall within the scope of the appended claims and their equivalents.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A support device for supporting a graft assembly within a vessel, wherein the graft assembly includes a tubular portion having a proximal end, said support device comprising:

attachment means for attaching the graft assembly to a vessel wall of the vessel, wherein said attachment means comprises at least one attachment assembly;

fastening means for fastening said attachment means to the vessel wall, wherein a portion of said fastening means penetrates said attachment means and the vessel wall and secures said attachment means to the vessel wall;

connecting means for connecting said attachment means to the proximal end of the graft assembly, whereby said attachment means is spaced from the proximal end of the graft assembly, wherein said connecting means includes a support system that extends from said attachment means to the proximal end of the graft assembly; and securing means for securing said connecting means to the proximal end of the graft assembly.

2. The support assembly according to claim 1, wherein said at least one attachment assembly includes at least one attachment pad.

3. The support assembly according to claim 1, wherein said at least one attachment assembly includes an attachment collar.

4. The support assembly according to claim 1, wherein said at least one attachment assembly is formed from a biocompatible material.

5. The support assembly according to claim 1, wherein said support assembly includes at least one support leg that extends from said attachment means to the proximal end of the graft assembly.

6. The support assembly according to claim 5, wherein said at least one support leg extends to said at least one attachment assembly.

7. The support assembly according to claim 6, wherein said attachment means includes a plurality of attachment assemblies, wherein said at least one support leg extends to each of said plurality of attachment assemblies.

8. The support assembly according to claim 7, wherein each of said at least one support leg is interconnected.

9. A graft repair system for use in the repair of aneurysm within a vessel, said graft repair system comprising:

a graft assembly having a tubular portion, proximal and distal ends, wherein said tubular portion extends between said proximal and distal ends; and a support device for supporting said graft assembly within the vessel, said support device including attachment means for attaching said graft assembly to a vessel wall of the vessel, wherein said attachment means comprises at least one attachment assembly; fastening means, wherein a portion of said fastening means penetrates said attachment means and the vessel wall and secures said attachment means to the vessel wall; connecting means for connecting said attachment means to said proximal end of said graft assembly, whereby said attachment means is spaced from said proximal end of said graft assembly, wherein said connecting means includes a support assembly that extends from said attachment means to said proximal end of said graft assembly, wherein said connecting means includes a support system that extends from said attachment means to said proximal end of said graft assembly; and securing means for securing said connecting means to said proximal end of said graft assembly.

10. The graft repair system according to claim 9, wherein said graft assembly is a bifurcated graft assembly.

11. The graft repair system according to claim 9, wherein said graft assembly further comprises a flexible distal attachment graft assembly for securing said distal end of said graft assembly to the vessel.

12. The graft repair system according to claim 9, wherein said at least one attachment assembly includes at least one attachment pad.

13. The graft repair system according to claim 9, wherein said at least one attachment assembly includes an attachment collar.

14. The graft repair system according to claim 9, wherein said at least one attachment assembly is formed from a biocompatible material.

15. The graft repair system according to claim 9, wherein said support assembly includes at least one support leg that extends from said attachment means to said proximal end of said graft assembly.

16. The graft repair system according to claim 15, wherein said at least one support leg extends to said at least one attachment assembly.

17. The graft repair system according to claim 16, wherein said attachment means includes a plurality of attachment assemblies, wherein said at least one support leg extends to each of said plurality of attachment assemblies.

18. The graft repair system according to claim 17, wherein each of said at least one support leg is interconnected.

\* \* \* \* \*